United States Patent [19]

Kauke

[11] Patent Number: 4,701,861

[45] Date of Patent: Oct. 20, 1987

[54] FILTER TEST DEVICE

[75] Inventor: Heinz Kauke, Erlensee, Fed. Rep. of Germany

[73] Assignee: Pall Corporation, Glen Cove, N.Y.

[21] Appl. No.: 739,445

[22] Filed: May 31, 1985

[51] Int. Cl.⁴ .............................................. G01M 3/20
[52] U.S. Cl. .................................... 364/502; 364/500;
364/572; 73/38; 73/40; 73/40.7; 210/359;
210/433.2; 210/321.72
[58] Field of Search ............... 364/572, 510, 502, 500;
73/38, 40, 40.7, 45.2; 210/359, 433.2

[56] References Cited

U.S. PATENT DOCUMENTS

| 4,336,590 | 6/1982 | Jacq et al. | 364/510 |
| 4,402,214 | 9/1983 | Morgan et al. | 73/38 |
| 4,449,392 | 5/1984 | Huschke | 73/40 |
| 4,515,007 | 5/1985 | Herman | 73/40.7 |

OTHER PUBLICATIONS

"Diffusion and Bubble Point Testing of Microporous Cartridge Filters: Electromechanical Methods", Olson et al., Journal of Parenteral Science and Technology, vol. 37, pp. 117-124, Jul.-Aug. 1983.
Palltronic, The New Standard in Filter Integrity Testing Pall Electronic Forward Flow Test Equipment (FFEL 706) The Pall Portable Bench Model Electronic Forward Flow Test Kit (FFEL 706).
Palltronic Integrity Test Kit FFE02, published by Pall Process Filtration Limited, Portsmouth, England.

Primary Examiner—Errol A. Krass
Assistant Examiner—V. N. Trans
Attorney, Agent, or Firm—Leydig, Voit & Mayer

[57] ABSTRACT

A filter test device comprises an inlet which communicates with a gas source, an outlet which communicates with the inlet of a filter vessel, a pneumatic valve apparatus disposed between the inlet and the outlet of the filter test device for regulating the flow of gas from the source to the filter vessel, an electronic controller for controlling the pneumatic valve apparatus in accordance with one of a plurality of sets of parameters and including a memory circuit for storing all of the sets of parameters, and a mechanism for selecting one set of parameters from all the sets of parameters stored in the memory circuit.

6 Claims, 5 Drawing Figures

FILTER TEST DEVICE

TECHNICAL FIELD

The present invention relates to a device for testing filter systems. In particular, it relates to a filter test device for implementing the testing process.

BACKGROUND ART

Frequently, the filtering of impurities and other contaminants from a liquid or gas is a critical step in a manufacturing process. For example, in the pharmaceutical industry, the failure of a filter to remove impurities may have potentially devastating effects on public health. Thus, manufacturers must continually test the integrity of the filters they are using to ensure that the filters are operating satisfactorily.

Many devices for testing filters are available on the market. For example, Pall Corporation markets a filter testing device styled as the Integrity Test Kit FFE02 under the trademark Palltronic. This Palltronic filter testing device automatically tests a filter by means of the well-known pressure hold test procedure. The parameters for the test are entered via a keyboard on the Palltronic apparatus and the test is then automatically performed. A printer on the Palltronic device furnishes a record of all key test parameters and a report of the results of the test.

DISCLOSURE OF THE INVENTION

It is an object of the present invention to provide an improved filter test device. Specific objects include providing a filter test device which not only minimizes the amounts of data that must be input into the device but also allows this data to be entered in a far more simple and reliable manner.

A filter test device according to the present invention may be incorporated in a filter testing arrangement which tests the integrity of one of several filter systems according to one of several sets of parameters, each set of parameters corresponding to a respective filter system. The testing arrangement includes a source of pressurized gas and each filter system includes a filter vessel containing one or more filter elements between an inlet and an outlet. The filter test device comprises an inlet which communicates with the gas source, an outlet which communicates with the inlet of the filter vessel, and a pneumatic valve apparatus disposed between the inlet and outlet for regulating the flow of gas from the gas source to the filter vessel. The filter testing device also comprises an electronic circuit for controlling the pneumatic valve apparatus in accordance with one of the sets of parameters. This electronic circuit includes a memory circuit for storing all of the sets of parameters. The filter test device further comprises a mechanism for selecting the one set of parameters from all the sets of parameters stored in the memory circuit. In this manner, the electronic circuit may control the pneumatic valve apparatus in accordance with the set of parameters corresponding to the filter system being tested.

In accordance with another aspect of the invention, the mechanism for selecting the set of parameters may be a card reading device for reading a magnetic label portion of the card which identifies the set of parameters corresponding to the filter system. The card reading device may also be able to write the test results in a magnetic tablet portion of the card. In this manner, data may be particularly reliably and easily entered into and obtained from the filter testing device.

BEST MODE FOR CARRYING OUT THE INVENTION

Figure 1:
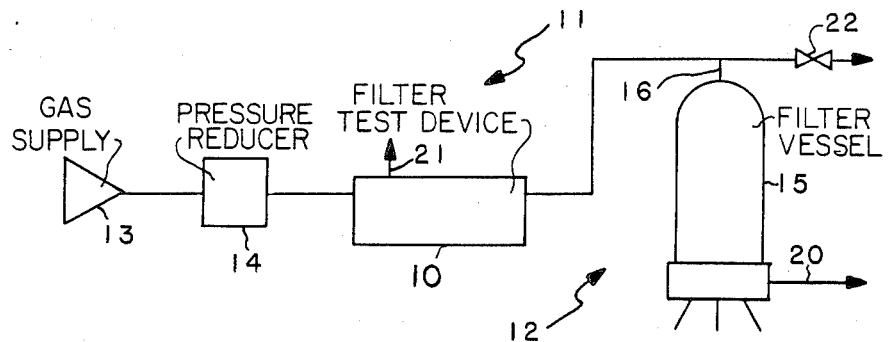
FIG. 1 is a block diagram of a filter testing arrangement incorporating an exemplary filter test device embodying the present invention.

As shown in FIG. 1, an exemplary microprocessor-controlled filter test device 10 constructed and operated according to the present invention may be incorporated in an arrangement 11 for testing the integrity of a filter system 12. Generally, the testing arrangement 11 comprises a pressurized gas supply 13 which feeds a gas via a pressure reducer 14 and the filter test device 10 to a filter system 12. The filter system 12 comprises a filter vessel 15 which serves as a container, containing one or more filter elements (not shown) to be tested between an inlet 16 and an outlet 20. The filter vessel 15 may comprise the housing in which the filter element or elements will eventually be used or a vessel especially designed for testing one or more filter elements. Although the filter vessel 15 may contain more than one filter element, for purposes of further describing the exemplary filter test device 10 it will be assumed that the filter vessel 15 contains only one filter element.

While the testing arrangement 11 may utilize any of several well known procedures for testing the integrity of the filter system 12, the exemplary filter test device 10 implements a test procedure commonly known as the pressure hold test. According to this test, the filter element is first wetted with a liquid, such as water. A suitable gas, such as compressed air or nitrogen, is then supplied by the gas supply 13 to the pressure reducer 14. The pressure reducer 14 reduces the pressure of the gas to a value preferably within a range from about 0.05 bar (0.73 psia) to about 6 bar (84 psia) and then supplies the gas to the filter test device 10.

Under control of the microprocessor-controlled filter test device 10, the filter vessel 15 is then filled with gas until the pressure of the gas on the upstream surface of the filter element reaches a desired test pressure. This test pressure may preferably be only slightly less than the critical pressure necessary to drive the liquid from the largest pores of the filter element and permit bulk flow of the gas through the filter element. For example, the exemplary filter test device 10 may supply gas to the filter vessel 15 until the test pressure at the upstream surface of the filter element is about 85 percent of the critical pressure.

Further according to the pressure hold test, once the test pressure is attained, the filter test device 10 isolates the filter system 12 from the gas supply 13 and monitors the system pressure upstream from the filter element. The integrity of the portion of the filter system 12 upstream from the filter element, including the filter element, any seals around the filter element, the filter vessel upstream from the filter element, and the inlet line 15, is indicated by the rate at which the pressure decays. If this upstream portion of the filter system 12 has no defects which would allow bulk gas flow, the pressure will decay relatively slowly due, for example, to diffusion of gas across the filter element via the liquid in the pores of the filter element. However, if this upstream portion of the filter system 12 is defective, the pressure will decay quickly as the gas flows through the defect. Once the pressure has been monitored for a sufficient amount of time to accurately indicate the integrity of the filter system 12, the gas in the filter vessel 15 is vented either automatically via a vent outlet 21 on the filter test device 10 or, for larger gas volumes, manually via a vent valve 22 on the filter vessel 15.

Figure 2:
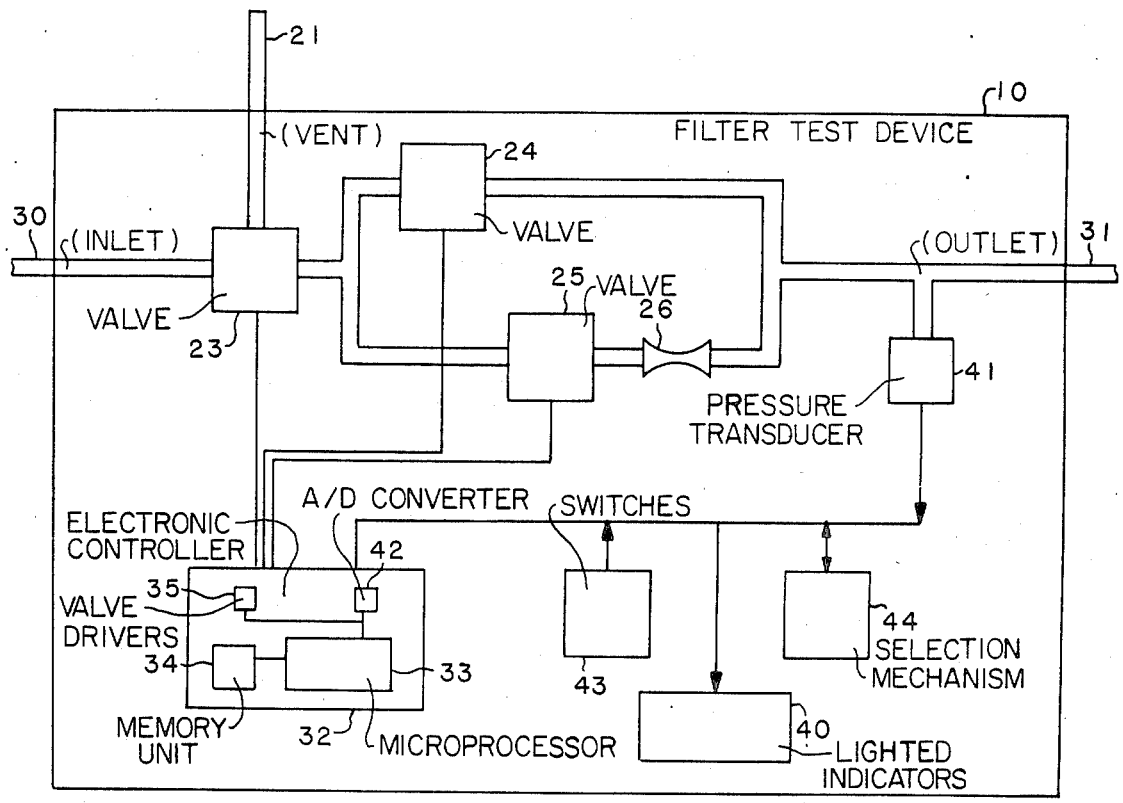
FIG. 2 is a block diagram of the exemplary filter test device of FIG. 1.

As shown in FIG. 2, the exemplary filter test device 10 comprises three magnetically-actuated control valves 23-25. A first control valve 23 permits gas intake from the pressure reducer 14 via an inlet 30 of the filter test device 10 or gas exhaust through the vent outlet 21. A second control valve 24 controls gas intake from the inlet 30 to the outlet 31 of the filter test device 10 and gas exhaust through the vent outlet 21, each via the first control valve 23. A third control valve 25 also allows gas to be supplied to the filter vessel 15 via the outlet 31. A throttle 26 together with the third control valve 25 controls the flow of gas into the filter vessel 15 so the test pressure is attained slowly in order to avoid inadvertently blowing the liquid from the pores of the filter element.

Each of the control valves 23-25 are controlled by an electronic controller 32 which may include a microprocessor 33, a memory unit 34, the appropriate driving system 35 for the valves and for certain lighted indicators 40, such as status lights and LED displays. Since the controller 32 monitors the vessel pressure via a pressure transducer 41, it may further include an A/D converter 42. Various switches 43, e.g., a power switch, a reset switch, and a recall switch, provide additional input to the controller 32.

In accordance with one aspect of the invention, the electronic controller 32 may store in the memory unit 34 several sets of parameters for the pressure hold test. The parameters of the pressure hold test differ from one filter system to another. These parameters, which include the value of the critical pressure, the rate at which the test pressure is attained, the amount of time that the vessel pressure is monitored, and the pressure decay limit, are dependent on such characteristics of the filter system as the pore size, chemical composition, and type of filter medium, e.g., microfibrous or membranous, of the filter element. Thus, a set of parameters for the pressure hold test must be provided for each different filter system. In the exemplary filter test device 10, the controller 32 may store a set of parameters for each of, for example, sixteen different filter systems.

In accordance with a further aspect of the invention, the filter test device 10 also includes a mechanism 44 which allows a user to select a particular set of parameters for a particular filter system. This mechanism 44 may be as simple as a group of switches, each switch corresponding to a different set of parameters. However, in the exemplary filter test device 10, the mechanism 44 preferably comprises a magnetic card reader/writer. A magnetic card (not shown) may then be provided for each filter system. The card may have a magnetic strip which includes a label portion having, for example, a code which identifies the set of parameters to be used in testing a particular filter system. The card reader/writer 44 may read the code and communicate this information to the controller 32 which, in turn, selects from the memory unit 34 the set of parameters identified by the code 95 the set of parameters to be used in testing the filter system. The magnetic strip may also include a tablet portion so that once the test has been completed, the controller 32 may direct the card reader/writer 44 to write the results of the test in the tablet portion of the card. In this manner, each different filter system may be identified with an appropriate set of parameters and each filter system may be readily associated with a card containing the test results for that filter system.

Figure 3A:
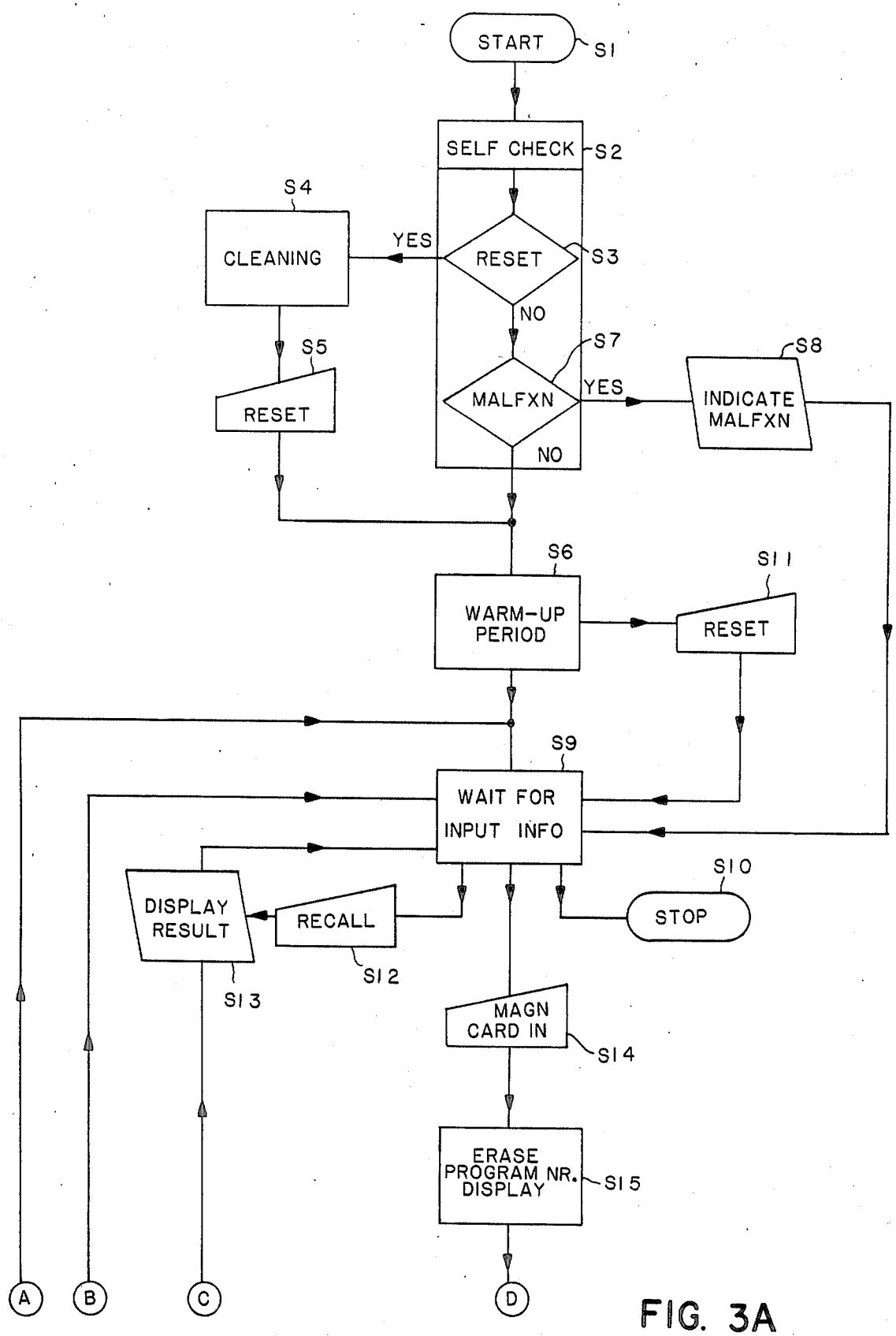
FIGS. 3A–C are a diagram of the preferred mode of operation of the filter test device of FIG. 2.
Figure 3B:
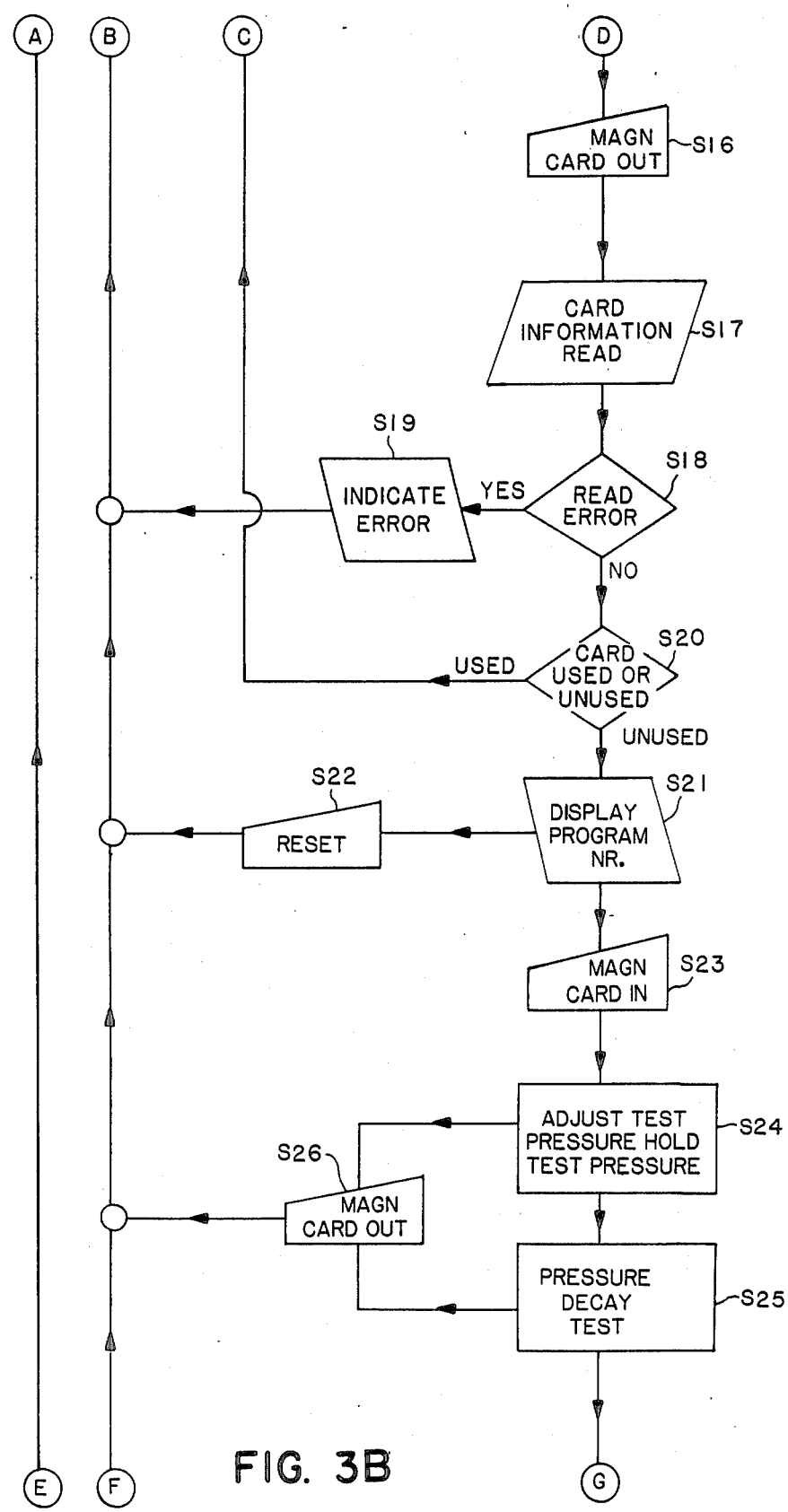
Figure 3C:
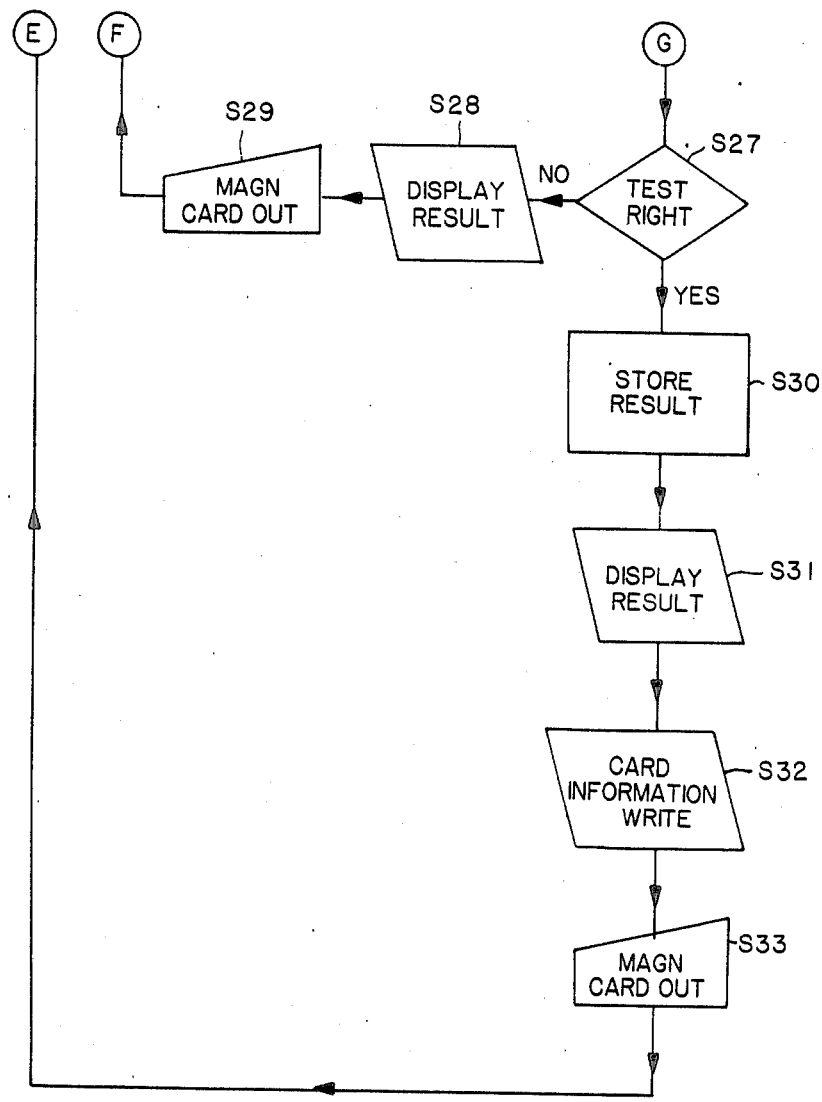

The microprocessor 33 of the exemplary filter test device 10 may be programmed according to a preferred mode of operation, as shown in FIG. 3. Initially, the filter test device 10 is energized S1 by activating the power switch, the power preferably being supplied by rechargeable batteries (not shown in FIG. 2) or any other portable power source. The filter test device 10 may then begin performing S2 certain self-diagnostic procedures. If the filter test device 10 determines S3 that the reset switch has been activated during these self-diagnostic procedures, it will begin performing S4 certain cleaning operations, which may be terminated by again activating S5 the reset switch. Once the cleaning operations are terminated, the filter test device 10 settles S6 into a warm-up period, which for the exemplary filter test device 10 may last about five minutes.

If the reset switch is not activated during the self-diagnostic procedures, the filter test device 10 will complete the procedures and determine S7 if any malfunction has occurred. If a malfunction has occurred, the filter test device 10 provides S8 a malfunction indication and then awaits S9 an input from the user. The user may then deactivate S10 the power switch and correct the malfunction. If no malfunction has occurred, the filter test device 10 settles S6 into the warm-up period. Any time during the warm-up period, the warm-up period may be aborted by activating S11 the reset switch.

Following the warm-up period, the controller 32 awaits S9 an input from the user. For example, the user may activate S12 the recall switch. The test results for the last test run by the filter test device 10, which are stored in the memory unit 34 after each test, will then be displayed S13 by the lighted indicators 40. The filter test device 10 will then await S9 another input from the user.

The user may also insert S14 a magnetic card in the card reader/writer 44 whereupon the lighted indicators 40 cease displaying S15 information related to previous tests. While the information on the card may be read any time after insertion, for the exemplary filter test device 10 the magnetic card must be withdrawn S16 from the card reader/writer 44 before the information on the card is read S17. This information is then checked S18 for errors according to any well-known error detecting procedure. If an error is detected, an error indication is provided S19 and the filter test device 10 again awaits S9 further input from the user. If no error is detected, the microprocessor 33 determines S20 whether or not the information read by the card reader/writer 44 includes any previous test results written in the tablet portion of the card. If previous test results are provided, they are displayed S13 and the filter test device 10 again awaits S9 input from the user. In this manner, the exemplary filter test device 10 provides a highly convenient procedure for informing the user of the results of previous tests.

If no previous test results are provided, the filter test device 10 displays S21 a code such as a program number which identifies the set of parameters specified by the card. If this set of parameters does not correspond to the filter system being tested, the user may avoid running the test by activating S22 the reset switch. Otherwise, the user may initiate the test by reinserting S23 the card. Once the test is initiated, the controller 32 switches the first control valve 23 to the vent outlet 21 and opens the second and third control valves 24, 25 so the filter system 12 may be vented through the vent outlet 21. The controller 32 then checks the zero point of the filter system 12, i.e., the signal from the pressure sensor 41 which corresponds to atmospheric pressure. Next, the controller 32 switches the first control valve 23 to the inlet 30, supplying S24 gas via the second and third control valves 24, 25 and the outlet 31 to the filter vessel 15. As the vessel pressure nears the test pressure specified by the set of parameters identified by the card, the controller 32 closes the second control valve 24. The gas then flows into the filter vessel 15 via throttle 26, which is fixed so the pressure in the filter vessel 15 slowly approaches the test pressure.

Once the test pressure is attained, the controller 32 closes the third control valve 25, isolating the filter vessel 15. The controller 32 also switches the first control valve 23 to the vent outlet 21. Consequently, during the test, only atmospheric pressures acts on the second and third control valves 24, 25. The vessel pressure as communicated to the outlet 31 of the filter test device 10 is then monitored S25 during the test by the controller 32 via the pressure sensor 41 for the period of time specified by the identified set of parameters. At the end of this period, the pressure decay may be recorded in the memory unit 34 and the controller 32 opens the second control valve 24, allowing the gas in the filter vessel 15 to be exhausted, i.e., vented, through the vent outlet 21.

Any time after initiation of the test, the test may be aborted by withdrawing S26 the magnetic card. The filter test device 10 will then await S9 furhter input from the user. The test will also be aborted if the controller 32 determines S27 that the test conditions cannot be attained, e.g., the test pressure cannot be attained due to a defect in the filter system. The controller 32 will display S28 the results of the test on the display indicators 40 but will not write the results on the tablet portion of the card. Consequently, the magnetic card may be withdrawn S29 and reused to initiated a test. Once the magnetic card is withdrawn the filter test device 10 will again await S9 input from the user.

If the test conditions are attained, the integrity of the filter system will be evaluated by comparing the pressure decay to the pressure decay limit specified in the identified set of parameters. The results of the evaluation and any other test results may then be stored S30 in the memory unit 34, displayed S31 on the display indicators 40, and written S32 on the magnetic tablet portion of the card. The card may then be withdrawn S33 and the filter test device 10 will again await S9 an input from the user, e.g., the user may deactivate S10 the power switch. In the exemplary filter test device 10, the card may never again be used to initiate a test, although the test results written on the card may be re-displayed at a later date.

While an exemplary filter test device embodying the invention has been previously described, the invention is not limited to that embodiment. Alternative embodiments and modifications which would still be encompassed by the invention may be made by those skilled in the art, particularly in light of the foregoing teachings. Therefore, the following claims are intended to cover any alternative embodiments, modifications or equivalents which may be included within the spirit and scope of the invention as claimed.

What is claimed is:

1. In an arrangement which test the integrity of one of a plurality of filter systems according to one of a plurality of sets of parameters wherein the arrangement includes a source of pressurized gas, each filter system includes a filter vessel containing at least one filter element between an inlet and an outlet, and each set of parameters corresponds to a respective filter system, a filter test device comprising an inlet communicating with the gas source, an outlet communicating with the inlet of the filter vessel, valve means disposed between the inlet and the outlet of the filter test device for regulating the flow of gas from the gas source to the filter vessel, circuit means for controlling the valve means in accordance with one of the sets of parameters, said circuit means including a memory means for storing the plurality of sets of parameters, and means communicating with the circuit means for selecting said one set of parameters whereby the circuit means controls the valve means in accordance with the set of parameters corresponding to the filter element contained in the filter system.

2. The filter test device according to claim 1 wherein the selecting means includes means for reading a label identifying said one set of parameters.

3. The filter test device according to claim 2 wherein the reading means comprises card reading means for reading a magnetic label portion of the card and wherein the selecting means further includes card writing means for writing in a magnetic tablet portion of the card.

4. In an arrangement which tests the integrity of one of a plurality of filter systems according to one of a plurality of sets of test parameters for a pressure hold test wherein the arrangement includes a source of pressurized gas, each filter system includes a filter vessel containing at least one wetted filter element between an inlet and an outlet, and each set of test parameters corresponds to a responsive filter system and includes a first value indicative of a test pressure and a second value indicative of a pressure decay limit, a filter test device comprising an inlet communicating with the gas source, an outlet communicating with the inlet of the filter vessel, valve means disposed between the inlet and the outlet of the filter test device for regulating the flow of gas from the gas source to the filter vessel, means for sensing the pressure at the outlet of the filter test device, circuit means for controlling the valve means in accordance with one set of test parameters, said circuit means communicating with the pressure sensing means and including memory means for storing the plurality of sets tests parameters means for controlling the valve means to yield a pressure at the outlet of the filter test device equal to the first value specified by the one set of test parameters, and means for evaluating the integrity of the filter system in accordance with the second value specified by the one set of test parameters, means communicating with the circuit means for reading a card which identifies as said one set of test parameters the set of test parameters stored in the memory means which corresponds to said one filter system.

5. The filter test device according to claim 4 wherein said card reading means includes means for reading a magnetic label portion of the card and wherein the filter test device further comprises means for writing the results of the evaluation in a magnetic tablet portion of the card.

6. The filter test device of claim 5 wherein the reading means further includes means for reading the magnetic tablet portion of the card and wherein the filter test device further comprises means for displaying said results written thereon.

* * * * *